United States Patent

Shih

[11] 4,203,902
[45] May 20, 1980

[54] PROCESS FOR PREPARING 6- AND 2-SUBSTITUTED-1-CARBADETHIAPEN-2-EM-3-CARBOXYLIC ACIDS

[75] Inventor: David H. Shih, Edison, N.J.
[73] Assignee: Merck & Co., Inc., Rahway, N.J.
[21] Appl. No.: 898,591
[22] Filed: Apr. 21, 1978
[51] Int. Cl.$^2$ .......................................... C07D 487/04
[52] U.S. Cl. ........................... 260/326.31; 260/326.22; 424/274; 560/16
[58] Field of Search ..................... 260/326.31; 424/274

[56] References Cited

U.S. PATENT DOCUMENTS

| | | | |
|---|---|---|---|
| 3,950,357 | 4/1976 | Kahan et al. | 260/326.31 |
| 4,013,648 | 3/1977 | Horning et al. | 260/326.31 |

OTHER PUBLICATIONS

Wong et al.; J.A.C.S. vol. 99, pp. 2823–2824 (1977).
Fieser et al., Advanced Organic Chemistry, p. 313 (1961).

*Primary Examiner*—Mary C. Lee
*Attorney, Agent, or Firm*—Hesna J. Pfeiffer; Julian S. Levitt; James A. Arno

[57] ABSTRACT

A process is disclosed for preparing antibiotic 6- and 2-substituted-1-carbadethiapen-2-em-3-carboxylic acids and their pharmaceutically acceptable salts and esters (I)

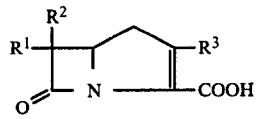

wherein: $R^1$ and $R^2$ are selected from hydrogen, alkyl aryl, and aralkyl; and $R^3$ is hydrogen, —R, —OR, or —SR, wherein R is hydrogen, alkyl, aryl or aralkyl. The process comprises complexing an appropriately substituted δ,ω-unsaturated amino acid with a transition metal carbonyl complex, followed by oxidatively induced ligand transfer and ring closure:

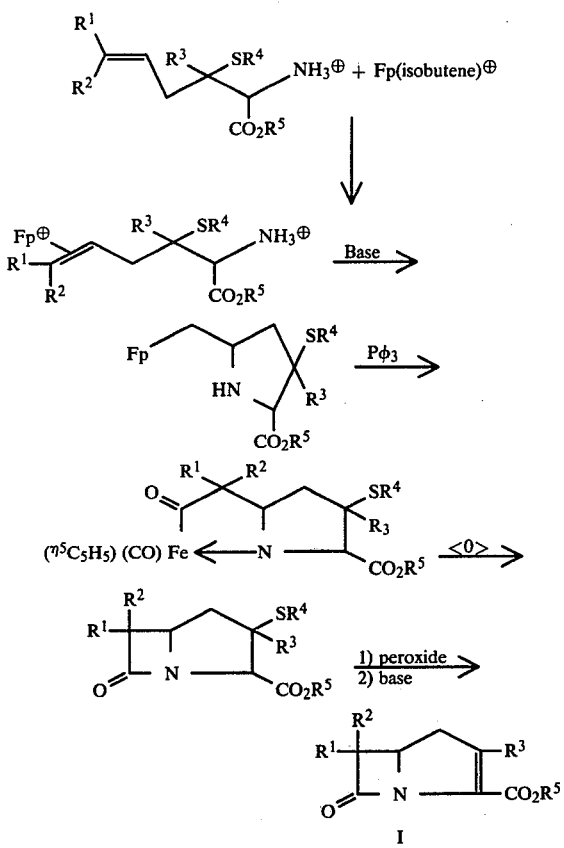

wherein: $F_p = \eta^5$—$C_5H_5Fe(CO)_2$ and $F_p$ (isobutene$^\oplus$) represents a cationic complex between $F_p$ and an olefin such as isobutene, which complex cation is employed in the initial ligand exchange reaction; $R^4$ is lower alkyl or phenyl; $R^5$ is a readily removable blocking group or pharmaceutically acceptable ester radical; and $R^1$, $R^2$ and $R^3$ are as defined above.

2 Claims, No Drawings

PROCESS FOR PREPARING 6- AND 2-SUBSTITUTED-1-CARBADETHIAPEN-2-EM-3-CARBOXYLIC ACIDS

BACKGROUND OF THE INVENTION

This invention relates to a process for preparing bicyclic, β-lactam antibiotics. Specifically it relates to preparing 6- and 2-substituted-1-carbadethiapen-2-em-3-caboxylic acids and their pharmaceutically acceptable salts and esters (I):

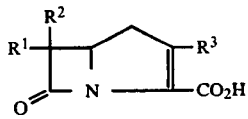

wherein, inter alia, $R^1$ and $R^2$ are independently selected from hydrogen, substituted and unsubstituted: alkyl, aryl, aralkyl, and $R^3$ is inter alia, selected from hydrogen, —R, —OR, —SR,; wherein R is substituted and unsubstituted: alkyl, aryl and aralkyl.

In general, the process of this invention provides the substituted carbapenem (I) via a transition metal carbonyl complex induced ring closure and carbonyl insertion of an appropriately substituted aminoalkene. This general reaction has been reported in the literature for the preparation of the unsubstituted, antibiotically inactive bicyclic β-lactams 4 and 7 [Wong, et al., J.A.C.S. 99 2823, (1977)]:

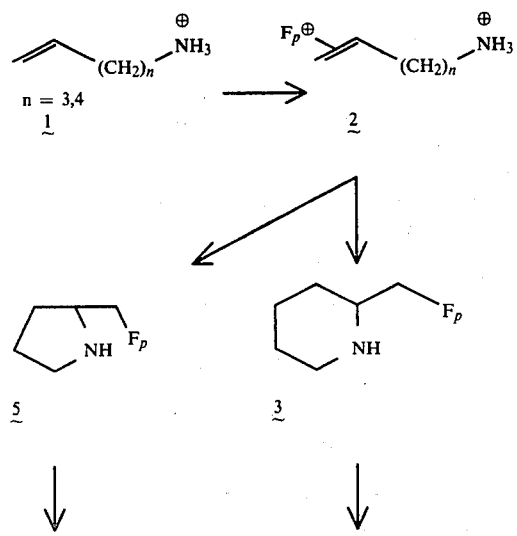

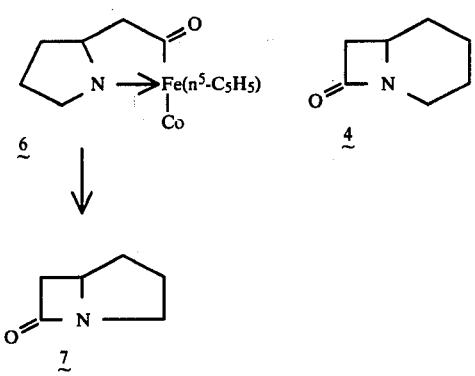

wherein: $F_p = \eta^5—C_5H_5Fe(CO)_2$. In the Wong, et al., scheme, the complex 2 is obtained from the olefinic amine by exchange reaction with $F_p$ (isobutene)tetrafluoroborate. Successive deprotonation with tri-n-butylamine followed by potassium tert-butoxide gives the piperidine complex 3, which is coverted with $Ag_2O$ (THF, 65° C., 20 h) to the lactam 4.

A similar sequence, employing 1-pentenylammonium tetrafluoroborate gives the pyrrolidine complex 5. An attempt to convert this directly to β-lactam by oxidation led instead to a polyamide ($v_{CO}$1590 cm$^{-1}$) due to the high reactivity of this lactam. However, when 5 was heated in THF for 4 h in the presence of 10 molar % of triphenylphosphine it was smoothly converted to the chelate 6 in 80% yield. Treatment of 6 with freshly precipitated $Ag_2O$ for 5 min. at 25° 1 C. led to the disappearance of chelate carbonyl absorptions and formation of β-lactam 7.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics and processes for their preparation continues.

Thus, it is an object of the present invention to provide a process for preparing the above-described carbapenems which are useful in animal and human therapy and in inanimate systems. These antibiotics are active against a broad range of pathogens which representatively include both gram positive bacteria such as *S. aureus*, *Strep. pyogenes*, and *B. subtilis*, and gram negative bacteria such as *E. coli*, Pseudomonas, *Proteus morganii*, Serratia, and Klebsiella.

DETAILED DESCRIPTION OF THE INVENTION

The process of the present invention can conveniently be summarized by the following diagram:

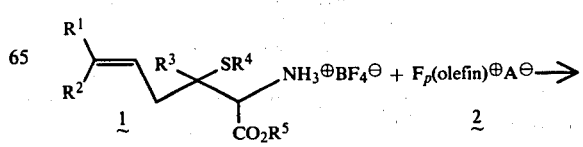

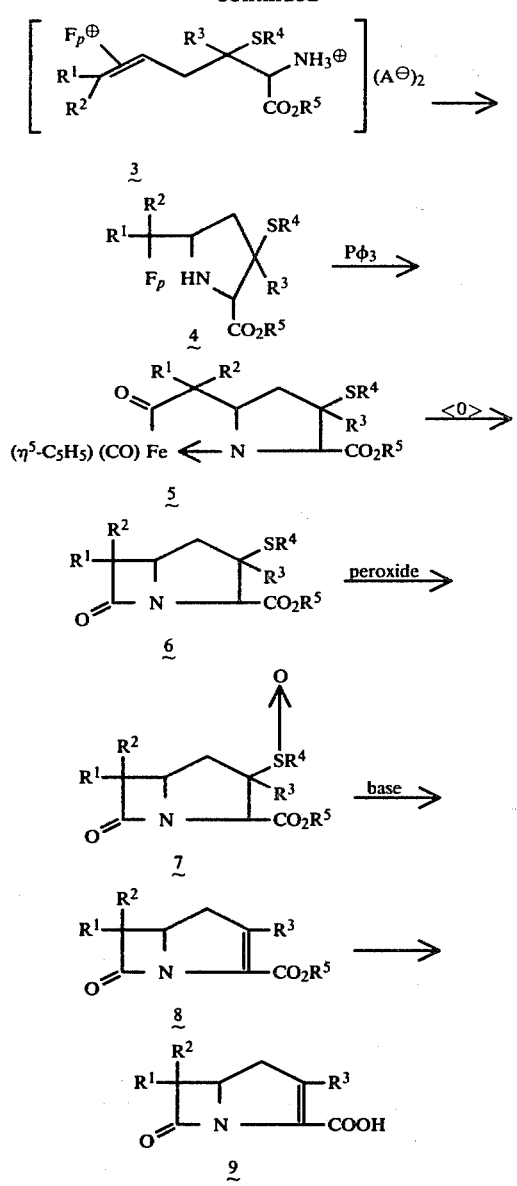

In words relative to the above diagram, 1, wherein A is a non-critical counter ion such as tetrafluoroborate, hexafluorophosphate, or the like, is exchanged with the complex 2 wherein the olefin is selected from the group consisting of isopropylene, ethylene, propylene, isobutylene and the like and $F_p$ is dicarbonyl $\eta^5$-cyclopentadienyl iron: $\eta^5$—$C_5H_5Fe(CO)_2$. The exchange reaction to provide complex 3 is conducted in a solvent such as THF, dioxane, DMF and the like at a temperature of from −20° to 100° C. for from 10 min. to 6 hours. The reaction 3→4 is accomplished by successive deprotonation. Ideally, the first deprotonation is accomplished with a base such as tri-n-butylamine, tri-isopropylamine, triethylamine or the like; the second deprotonation step, to abstract the pyrrolidine proton, is accomplished with one equivalent of a base such as potassium t-butoxide, sodium methoxide, lithium ethoxide or the like. Such deprotonations are conducted in the same solvent used in the initial exchange reaction. The reaction 4→5 is accomplished by treating 4 with a catalytic amount (10 to 20 molar %) of a triorganophosphine such as triphenylphosphine, tri-n-butylphosphine, tri-p-tolylphosphine or the like in a solvent such as THF, DME, ether, dioxane or the like at a temperature of from 40° to 100° C. for from 1 to 10 hours. Intermediate 5 is oxidized with from 1 to 2 equivalents of an oxidizing agent such as silver (I) oxide, copper (II) oxide, lead dioxide, chlorine or the like in a solvent such as THF, nitromethane, ether, DME or the like at a temperature of from −40° to 100° C. for from 0.5 to 6 hours to provide 6. A second oxidation [6→7] is conducted preferably with an oxidizing agent such as m-chloroperbenzoic acid, hydrogen peroxide, perbenzoic acid, peracetic acid or the like in a solvent such as THF, methylene chloride, nitromethane or the like at a temperature for from −10° to 60° C. for from 0.1 to 4 hours. The resulting sulfoxide (7) is treated with a base such as triethylamine, piperidine, pyridine, diisopropylamine or the like in a solvent such as THF, methylene chloride, acetonitrile, nitromethane or the like at a temperature of from 0° to 60° C. for from 0.1 to 4 hours to provide the unsaturated species 8, which species, when $R^5$ is a readily removable protecting group such as benzyl, p-nitrobenzyl, o-nitrobenzyl, p-methoxylbenzyl or the like, is deblocked by hydrogenolysis in a solvent such as ethylacetate, dioxane, dioxane/buffer or the like in the presence of a metal catalyst such as palladium on carbon, platinum, $RhCl(CO)_2\phi$ or the like under a hydrogen pressure of 1 to 40 atmospheres at 0° to 60° C. for from 0.1 to 6 hours. It should be noted that in above reaction diagram, $R^5$ may be hydrogen. Thus, protection, though preferred, is not required. Also $R^5$ may be a pharmaceutically effective ester radical such as pivaloyloxymethyl, p-t-butylbenzyl, 3-methyl-3-butenyl, phenyl or the like in which case the final deblocking reaction 8→9 is not necessary.

The compounds made available by the present invention are valuable antibiotics active against various gram-positive and gram-negative bacteria and, accordingly, find utility in human and veterinary medicine. Such sensitive bacteria representatively include: *Staphylococcus aureus, Escherichia coli, Klebsiella pneumoniae Serratia, Salmonella typhosa, Pseudomonas* and *Bacterium proteus*. The resulting compounds may further be utilized as additives to animal feed, for preserving foodstuffs, and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example, in waterbased paints and in the white water of paper mills to inhibit the growth of harmful bacteria.

These antibiotics may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maize-starch, calcium phosphate, sorbitol or glycine;

lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, or syrups; or may be presented as a dry product, for reconstitution with water or other suitable vehicles before use. Such liquid preparations may contain conventional additives such as suspending agents, for example, sorbitol, syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid.

Compositions for injection may be presented in unit dose form in ampules, or in multidose container. The compositions may take such forms as suspensions, solutions, or emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops, etc. Topical applications may be formulated in hydrophobic or hydrophilic bases as ointments, creams, or lotions.

Also, in addition to a carrier, the instant compositions may include other ingredients such as stabilizers, binders, antioxidants, preservatives, lubricators, suspending agents, viscosity agents or flavoring agents and the like. In addition, there may also be included in the compositions other active ingredients to provide a broader spectrum of antibiotic activity.

For veterinary medicine the composition may, for example, be formulated as an intramammary preparation in either long or quick-release bases.

The dosage to be administered depends to a large extent upon the general health and weight of the subject being treated, and the route and frequency of administration—the parenteral route being preferred for generalized infections and the oral route for intestinal infections. In general, a daily oral dosage consists of from about 2 to about 600 mg. of active ingredient per kg. of body weight of the subject in one or more applications per day. A preferred daily dosage for adult humans lies in the range of from about 15 to 150 mg. of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from about 15 mg. to about 1500 mg. of the active ingredient; however, in general, it is preferably to employ a dosage amount in the range of from about 100 mg. to 1000 mg. In parenteral administration the unit dosage is usually the pure compound in a slightly acidified sterile water solution or in the form of a soluble powder intended for solution.

The following Examples further illustrate the process of the present invention. All temperatures are given in °C.

EXAMPLE 1

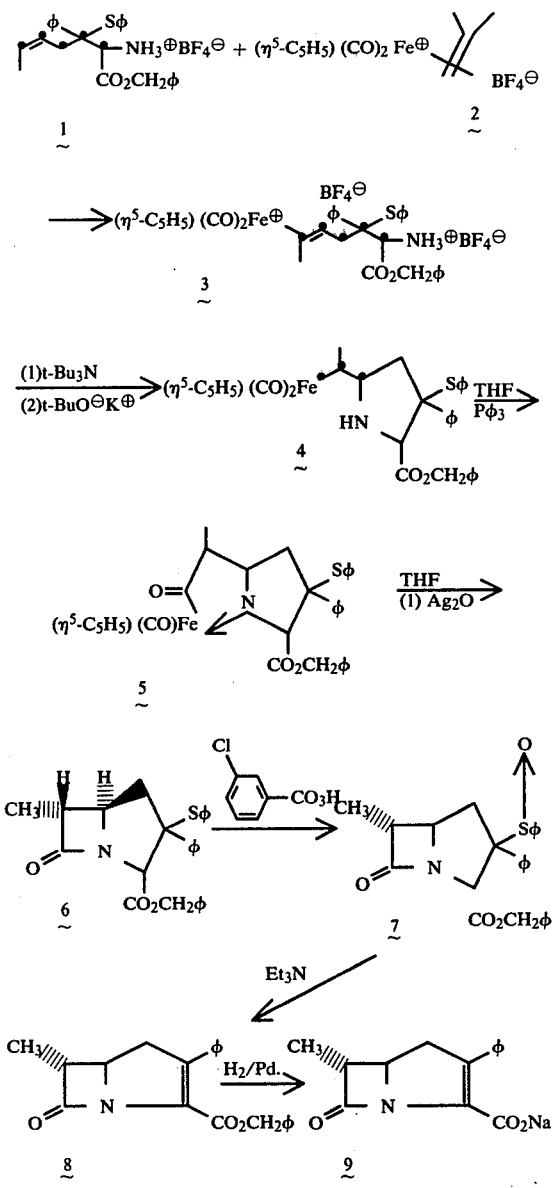

The ammonium tetrafluoroborate species (1) (10 mmol) is treated with isobutene iron complex (2) (10 mmol) in 50 ml THF for 1 hr at 25° C. To the mixture is added tri-n-butylamine (10 mmol); the mixture is stirred for 10 min at 25° C. followed by the addition of potassium t-butoxide (10 mmol); stirring is continued for 15 min. at 25° C. The resulting mixture containing the pyrrolidine complex (4) is treated with triphenylphosphine (1 mmol) for 4 hr at reflux. The pyrrolidine chelate (5) so obtained is mixed with freshly precipitated Ag$_2$O (10 mmol) for 5 min. at 25° 1 C. to yield the bicyclic β-lactam (6) which is oxidized with m-chloroperbenzoic acid (10 mmol) for 10 min at 25° C. to give the sulfoxide (7). Treatment of (7) with triethylamine (10 mmol) for 20 min. at 25° C. gives the desired 2-phenyl-6α-methyl-1-carbapenem benzyl ester (8). To the solution of (8) is added 50 ml water and NaHCO₃ (10mmol) then the mixture is subjected to hydrogenolysis under 40 psi H₂ in the presence of 10% Pd/C (2 mmol) for 3 hr at 25° C. to give the crude sodium salt of 2-phenyl-6α-methyl-1-carbapenem (9). The product 9 is purified by an XAD-2 column (1"×12") which is eluted with water then 10% THF/water to give, after lyophilization, 9.

EXAMPLE 2

Preparation of 1:

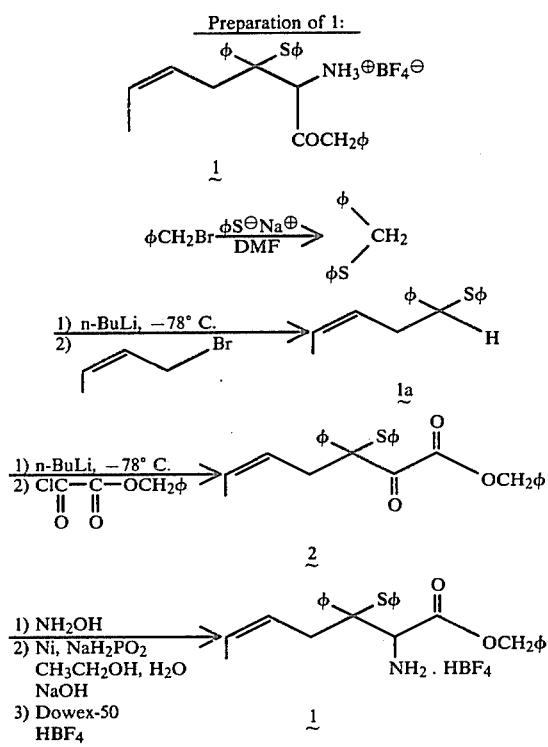

Benzyl bromide (10 mmol) in 30 ml DMF is treated with sodium thiophenoxide (10 mmol) for 6 hr at 60° C.; the mixture is then evaporated to dryness in vacuo. The residue is taken up with methylene chloride and washed with water. The organic layer is separated, dried over sodium sulfate and chromatographed by a silica gel column (1'×10"), eluting with 10% ethylacetate/cyclohexane to give the expected phenylthiophenylmethane. Treatment of phenylthiophenylmethane with n-bytyllithium (10 mmol) in 30 ml tetrahydrufuran (THF) at −78° C. for 10 min is followed by addition of allylbromide (10 mmol) and stirred for 1 hr at 25° C. The resulting mixture containing (1a) is again chilled to −78° C. and treated with n-butyllithium (10 mmol) for 10 min then benzyloxalylchloride (10 mmol) for 1 hr at 25° C. to give (2) which is isolated by a silica gel column (4×20 cm), eluting with 50% EtOAc/50% CH₂Cl₂. Treatment of 2 with hydroxyamine (10 mmol) for 1 hr at 25° C. followed by reduction with Raney nickel (1 mmol) in 1 N sodium hypophosphite (20 ml), 1 N NaOH (20 ml) and 30 ml ethanol for 3 hr at 25° C. yields the amine ester, which is purified by a Dowex - 50 column (4 cm×20 cm), eluting with 0.1 N HBF₄. On lyophilization of the resulting eluate, compound 1 is obtained.

What is claimed is:

1. A process for preparing:

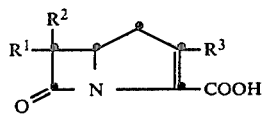

wherein $R^1$ and $R^2$ are independently selected from hydrogen, alkyl and hydroxyl-substituted alkyl having 1 to 6 carbon atoms, benzyl, and phenyl; $R^3$ is hydrogen, —R, —OR, and —SR wherein R is hydrogen and substituted and unsubstituted: alkyl having 1–6 carbon atoms, phenyl, and benzyl wherein the substituent is amino; consisting of treating:

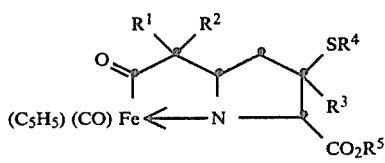

with an oxidizing agent selected from Ag₂O, CuO, PbO₂, or Cl₂ to yield:

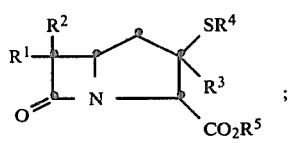

followed by treating with an oxidizing agent selected from m-chloroperbenzoic acid, H₂O₂, perbenzoic acid or peracetic acid to yield:

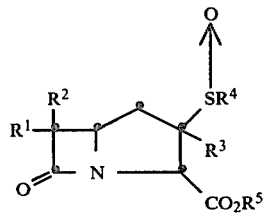

which is treated with base selected from triethylamine, piperidine, pyridine, or diisopropylamine to yield:

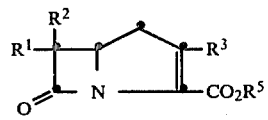

wherein: $R^4$ is phenyl and $R^5$ is hydrogen or benzyl; when $R^5$ is benzyl, the benzyl group is removed by hydrogenolysis to yield the free acid.

2. The process of claim 1 wherein $R^1$ is hydrogen; $R^2$ is methyl, hydroxymethyl, or 1-hydroxyethyl; and $R^3$ is phenyl or 2-aminoethylthio.

* * * * *